(12) United States Patent
Mazzocchi

(10) Patent No.: US 6,168,622 B1
(45) Date of Patent: Jan. 2, 2001

(54) METHOD AND APPARATUS FOR OCCLUDING ANEURYSMS

(75) Inventor: Rudy Mazzocchi, Merritt Island, FL (US)

(73) Assignee: Microvena Corporation, White Bear Lake, MN (US)

( * ) Notice: Under 35 U.S.C. 154(b), the term of this patent shall be extended for 0 days.

(21) Appl. No.: 09/119,823

(22) Filed: Jul. 21, 1998

Related U.S. Application Data

(63) Continuation of application No. PCT/US96/00893, filed on Jan. 24, 1996.

(51) Int. Cl.[7] .................................................. A61M 29/00
(52) U.S. Cl. ............................................ 623/1.2; 606/200
(58) Field of Search .......................... 623/1, 12; 606/195, 606/200

(56) References Cited

U.S. PATENT DOCUMENTS

| 2,281,448 | 4/1942 | Mathey . |
| 3,334,629 | 8/1967 | Cohn . |

(List continued on next page.)

FOREIGN PATENT DOCUMENTS

| 2 821 048 | 11/1979 | (DE) . |
| 233 303 A1 | 12/1984 | (DE) . |
| 0 380 666 B1 | 9/1988 | (EP) . |
| 0 547 530 A1 | 12/1992 | (EP) . |
| 2 527 301 | 11/1983 | (FR) . |
| 2 641 692 | 1/1989 | (FR) . |
| 93/10714 | 11/1992 | (WO) . |
| 94/06372 | 9/1993 | (WO) . |

OTHER PUBLICATIONS

Castaneda, et al., Migration of a Kimray–Greenfield Filter to the Right Ventricle, *Radiology*, Dec. 1983, pp. 687–690.

Allison, et. al., Article entitled: Therapeutic Embolization, *British Journal of Hospital Medicine*, Dec. 1978.

Duerig, Superelastic Nitinol for Medical Devices, *Medical Plastics and Biomaterials*, vol. 4, No. 2, Mar./Apr. 1997, pp. 30–43.

Dotter, "Transluminally–placed Coilspring Endarterial Tube Grafts, Long–term Patency in Canine Popliteral Artery," *Investigative Radiology*, vol. 4, Sep./Oct. 1969, pp. 329–332.

Dotter, et al., "Transluminal Expandable Nitinol Coil Stent Grafting: Preliminary Report," *Radiology*, vol. 147, Apr. 1983, pp. 259–260.

Schatz, et al., "Balloon–expandable Intracoronary Stents in the Adult Dog," *Circulation*, vol. 76, No. Aug. 1987, pp. 450–457.

Sweden Now, "When Hope is in Vein," 1988.

Palmaz, et al.., "Atherosclerotic Rabbit Aortas: Expandable Intraluminal Grafting," *Radiology*, 1986, pp. 723–726.

Rosseau, et al.., "Self–expanding Endovascular Prosthesis: An Experimental Study," *Radiology*, vol. 164, 1987, pp. 709–714.

Duprat, Jr., et al., "Self–expanding Metallic Stents for Small Vessels: An Experimental Study," *Radiology*, vol. 162, 1987, pp. 469–472.

Palestrant, et al., Comparative In Vitro Evaluation of the Nitinol Inferior Vena Cava Filter, *Radiology*, vol. 145, No. 2, Nov. 1982, pp. 351–355.

*Primary Examiner*—Michael J. Milano
(74) *Attorney, Agent, or Firm*—Nawrocki, Rooney & Sivertson, P.A.

(57) ABSTRACT

An aneurysm occlusion device has a bulbous body portion and an anchor. The body portion is sized to be received within an aneurysm and the anchor is sized and shaped to engage an interior surface of the vessel's wall. The body portion and the anchor are integrally formed of a resilient fabric permitting the occlusion device to be collapsed for deployment and resiliently self-expanded to include the aneurysm.

6 Claims, 5 Drawing Sheets

U.S. PATENT DOCUMENTS

| | | |
|---|---|---|
| 3,540,431 | 11/1970 | Mobin-Uddin . |
| 3,868,956 | 3/1975 | Alfidi et al. . |
| 3,952,747 | 4/1976 | Kimmell, Jr. . |
| 3,996,938 | 12/1976 | Clark, III . |
| 4,425,908 | 1/1984 | Simon . |
| 4,494,531 | 1/1985 | Gianturco . |
| 4,503,569 | 3/1985 | Dotter . |
| 4,553,545 | 11/1985 | Maass et al. . |
| 4,572,186 | 2/1986 | Gould et al. . |
| 4,619,246 | 10/1986 | Molgaard-Nielsen et al. . |
| 4,643,184 | 2/1987 | Mobin-Uddin . |
| 4,649,922 | 3/1987 | Wiktor . |
| 4,650,466 | 3/1987 | Luther . |
| 4,655,771 | 4/1987 | Wallsten . |
| 4,655,772 | 4/1987 | De Liotta et al. . |
| 4,665,906 | 5/1987 | Jervis . |
| 4,681,110 | 7/1987 | Wiktor . |
| 4,690,684 | 9/1987 | McGreevy et al. . |
| 4,699,611 | 10/1987 | Bowden . |
| 4,723,549 | 2/1988 | Wholey et al. . |
| 4,727,873 | 3/1988 | Mobin-Uddin . |
| 4,732,152 | 3/1988 | Wallsten et al. . |
| 4,733,665 | 3/1988 | Palmaz . |
| 4,793,348 | 12/1988 | Palmaz . |
| 4,794,928 | 1/1989 | Kletschka . |
| 4,800,882 | 1/1989 | Gianturco . |
| 4,817,600 | 4/1989 | Herms et al. . |
| 4,830,003 | 5/1989 | Wolff et al. . |
| 4,832,055 | 5/1989 | Palestrant . |
| 4,848,343 | 7/1989 | Wallsten et al. . |
| 4,856,516 | 8/1989 | Hillstead . |
| 4,873,978 | 10/1989 | Ginsburg . |
| 4,886,062 | 12/1989 | Wiktor . |
| 4,921,484 | 5/1990 | Hillstead . |
| 4,935,068 | 6/1990 | Deurig . |
| 4,969,891 | 11/1990 | Gewertz . |
| 4,984,581 | 1/1991 | Stice . |
| 4,990,156 | 2/1991 | Lefebvre . |
| 4,991,602 | 2/1991 | Amplatz et al. . |
| 4,998,539 | 3/1991 | Delsanti . |
| 5,002,560 | 3/1991 | Machold et al. . |
| 5,016,808 | 5/1991 | Heil, Jr. et al. . |
| 5,026,377 | 6/1991 | Burton et al. . |
| 5,034,001 | 7/1991 | Garrison et al. . |
| 5,041,093 | 8/1991 | Chu . |
| 5,053,008 | 10/1991 | Bajaj . |
| 5,059,205 | 10/1991 | El-Nounou et al. . |
| 5,067,489 | 11/1991 | Lind . |
| 5,067,957 | 11/1991 | Jervis . |
| 5,098,776 | 3/1992 | Kobayashi et al. . |
| 5,108,418 | 4/1992 | Lefebvre . |
| 5,108,419 | 4/1992 | Reger et al. . |
| 5,133,733 | 7/1992 | Rasmussen et al. . |
| 5,152,777 | 10/1992 | Goldberg et al. . |
| 5,190,546 | 3/1993 | Jervis . |
| 5,192,301 | 3/1993 | Kamiya et al. . |
| 5,221,261 | 6/1993 | Termin et al. . |
| 5,246,445 | 9/1993 | Yachia et al. . |
| 5,256,146 | 10/1993 | Ensminger et al. . |
| 5,334,217 | 8/1994 | Das . |
| 5,354,310 | 10/1994 | Garnic et al. . |
| 5,382,259 | 1/1995 | Phelps et al. . |
| 5,383,892 | 1/1995 | Cardon et al. . |
| 5,417,708 | 5/1995 | Hall et al. . |
| 5,421,955 | 6/1995 | Lau et al. . |
| 5,496,277 | 3/1996 | Termin et al. . |
| 5,496,332 | 3/1996 | Sierra et al. . |
| 5,514,115 | 5/1996 | Frantzen et al. . |
| 5,527,338 | 6/1996 | Purdy . |
| 5,562,726 * | 10/1996 | Chuter ........................................ 623/1 |
| 5,597,378 | 1/1997 | Jervis . |
| 5,662,671 | 9/1997 | Barbut et al. . |
| 5,690,671 | 11/1997 | McGurk et al. . |
| 5,725,552 | 3/1998 | Kotula et al. . |

* cited by examiner

METHOD AND APPARATUS FOR OCCLUDING ANEURYSMS

RELATED APPLICATIONS

This is a continuation of International Application No. PCT/US96/00893, filed Jan. 24, 1996, the teachings of which are incorporated herein by reference. Co-pending U.S. patent application Ser. No. 08/748,066, filed Nov. 12, 1996, is a continuation of U.S. patent application Ser. No. 08/272,425, filed Jul. 8, 1994, and the teachings of both of these applications are also incorporated herein by reference.

FIELD OF THE INVENTION

The present invention generally relates to intravascular devices for treating certain medical conditions and, more particularly, provides a method of forming intravascular devices and certain novel intravascular occlusion devices. The devices made in accordance with the invention are particularly well suited for delivery through a catheter or the like to a remote location in a patient's vascular system or in analogous vessels within a patient's body.

BACKGROUND OF THE INVENTION

A wide variety of intravascular devices are used in various medical procedures. Certain intravascular devices, such as catheters and guidewires, are generally used simply to deliver fluids or other medical devices to specific locations within a patient's body, such as a selective site within the vascular system. Other, frequently more complex, devices are used in treating specific conditions, such as devices used in removing vascular occlusions or for treating septal defects and the like.

One common ailment increasingly being treated by minimally invasive transcatheter techniques is an aneurysm. Generally, an aneurysm is defined by a dilation of an artery or other vessel. Although aneurysms are sometimes referred to as only arterial phenomenon, as used herein, an aneurysm can occur in other channels in a patient's body, such as veins or the like. The most common type of aneurysm is probably an arteriosclerotic aneurysm. Such aneurysms typically occur in larger arteries in the elderly due to weakening of the vessel walls by advanced cases of atherosclerosis.

Aneurysms are typically classified as being either axial or lateral. Axial aneurysms tend to involve the entire circumference of the blood vessel, causing an otherwise generally cylindrical length of the vessel to balloon outward. A lateral aneurysm is a distension of only one side of the vessel, typically taking the form of a saclike recess communicating with the lumen of the vessel. Such aneurysms are also referred to as "saccular" or "sacculated" aneurysms.

Aneurysms can occur at a variety of locations in a patient's vascular system. For example, an abdominal aortic aneurysm is a relatively common type of aneurysm which involves a distension of the aorta, e.g. in the vicinity of the iliac arteries and inferior mesenteric artery. Cardiac aneurysms, which are bulges in a weakened ventricular wall, typically arise as a result of a myocardial infarction. So-called "berry" aneurysms are small, saccular aneurysms of cerebral arteries, which frequently resemble a small berry.

In the past, aneurysms were frequently treated by direct surgical intervention. For example, to treat a lateral aneurysm in a vessel in the abdominal cavity, a surgeon can simply open the abdominal cavity and physically install a clamp around the base of the aneurysm to prevent, or at least limit, communication of blood between the aneurysm and the lumen of the vessel. This relieves pressure on the aneurysm, causing it to shrink. This could be very problematic for treating certain types of aneurysms, such as Cardiac aneurysms or cerebral berry aneurysms, due to the difficulty of safely accessing and surgically treating the aneurysm.

More recently, attempts have been made to develop minimally invasive techniques for treating aneurysms. Axial aneurysms in larger vessels are frequently treated by using stents and grafts. These devices basically reline the lumen of the vessel to provide some structural integrity and, in many cases, act as a prosthetic replacement for the affected length of the vessel. In some cases, the graft is relatively nonporous, enabling it to define a new lumen essentially as soon as it is in place in the vessel. More porous grafts and stents can also be employed as they can reduce pressure on the aneurysm and, long-term, provide a framework for endothelial ingrowth which allows the define a new, stronger vessel wall.

It is also possible to treat a lateral aneurysm with a graft or stent in much the same fashion that one treats an axial aneurysm. In such a circumstance, the graft occludes the neck of the aneurysm, or at least reduces blood flow into the aneurysm through the neck. Effectively stenting or occluding the neck helps reduce the size of the aneurysm and the likelihood that the aneurysm will rupture.

One disadvantage of using a graft in a circumstance such as this, though, is that the graft lines substantially more of the vessel than is necessary. This places a significant surface area of the graft into direct contact with stronger, healthier tissue of the vessel wall. Although the exact mechanisms are not well understood, it appears that this contact between a stent or graft and the vessel wall can cause neointimal hyperplasia and other ailments of the tissue of the vessel wall. Due to the potential for such collateral tissue damage, stents and grafts may be less desirable for use in treating lateral aneurysms than they are for axial aneurysms.

Current techniques for minimally invasive treatment of lateral aneurysms also include processes for filling the aneurysm. Such techniques usually involve either the placement of an expandable balloon in the aneurysm or filling the aneurysm with a thrombolytic agent or structure. For example, detachable occlusion balloons have been used for a number of medical procedures. These balloons are carried at the end of a catheter and, once inflated, can be detached from the catheter. Such a balloon may be positioned within an aneurysm, filled and then detached from the catheter. Deploring the balloon within the aneurysm can be rather difficult due to the high rates of blood flow through the aneurysm.

Once in place, the operator typically fills these balloons with a fairly solid medium, such as biocompatible plastic beads, helically wound coils or the like. Once the balloon is filled to substantially fill the aneurysm, the balloon will substantially reduce the stresses on the vessel wall and reduce the tendency of the aneurysm to rupture.

The other technique for filling lateral aneurysms involves placing within the aneurysm structure which will tend to thrombose and fill the aneurysm over a relatively short period of time. For example, one can take a fairly long, helically wound coil and shove the coil so that it is packed within the aneurysm. Over time, clot will tend to develop around the coil and effectively occlude the aneurysm. his process may be enhanced by increasing the surface area of the coils, such as by having strands of polyethylene extending outwardly from the surface of the coil. Such a product is commercially available from Target Therapeutics.

Such aneurysm filling techniques have their problems, as well. In deploying these devices, it is frequently difficult to keep them within the aneurysm. They be dislodged during the sometimes lengthy deployment process, but one can frequently retract or retrieve them rather than allowing them to float in the bloodstream and, potentially, embolize a vessel downstream. Even after they are deployed, though, they can still present some risks. When the balloon is filled, for example, an operator does not want to overfill the balloon due to the possible risk that the pressure of the balloon will rupture the aneurysm. Accordingly, the balloon may be slightly too small, potentially releasing the balloon from the aneurysm into the bloodstream. To avoid this risk, an operator may also deploy a stent or graft in the vessel to keep the articles filling the aneurysm in place, giving rise to the same problems noted above in connection with the discussion of such treatments.

SUMMARY OF THE INVENTION

The present invention provides a method for forming aneurysm occlusion devices from a resilient metal fabric and certain aneurysm occlusion devices which can be formed in accordance with this method. In the method of the invention, a metal fabric formed of a plurality of resilient strands is provided, with the wires being formed of a resilient material which can be heat treated to substantially set a desired shape. This fabric is then deformed to generally conform to a molding surface of a molding element and the fabric is heat treated in contact with the surface of the molding element at an elevated temperature. The time and temperature of the heat treatment is selected to substantially set the fabric in its deformed state. After the heat treatment, the fabric is removed from contact with the molding element and will substantially retain its shape in the deformed state. The fabric so treated defines an expanded state of a medical device which can be deployed through a catheter into a channel in a patient's body.

In accordance with an alternative embodiment of a method of the invention, an aneurysm in a channel in a patient's body may be identified and its general dimensions may be determined. A distal end of a catheter can be positioned adjacent the aneurysm; the distal end of the catheter may optimally be positioned within the aneurysm. An aneurysm occluder of the invention having appropriate dimensions for the aneurysm to be treated can be selected, whereupon it is collapsed and inserted into the lumen of the catheter. The occluder is urged through the catheter and out the distal end, whereupon it will tend to return to its expanded state. A body portion of the occluder is thereby positioned within the aneurysm itself. The rest of the occluder is deployed such that a central portion is positioned in or adjacent the neck of the aneurysm and an anchor is positioned within the lumen of the vessel.

Further embodiments of the present invention also provide specific aneurysm occlusion devices which may be made in accordance with the present invention. Such devices of the invention are formed of a metal fabric and have an expanded configuration and a collapsed configuration. The devices are collapsed for deployment through a catheter and, upon exiting the distal end of the catheter in a patient's channel, will resiliently substantially return to their expanded configuration.

In accordance with a first of these embodiments, an aneurysm occlusion device has an anchor sized to be received within a lumen of a vessel. A differently sized, preferably larger, body portion is connected to the anchor by means of a central portion. The body portion and the anchor desirably are larger than the neck of the aneurysm which the device is to occlude; the central portion of the occluder is preferably no larger than, and ideally is smaller than, the neck of the aneurysm.

DETAILED DESCRIPTION OF THE PREFERRED EMBODIMENTS

Figure 1B:
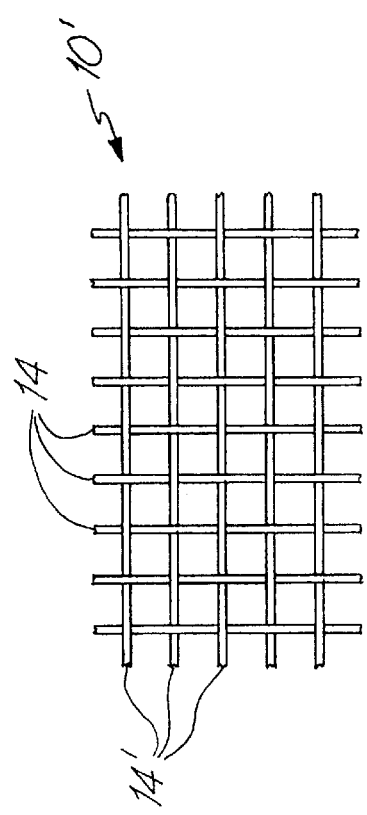
FIGS. 1A and 1B each depict a metal fabric suitable for use with the invention.
Figure 1A:
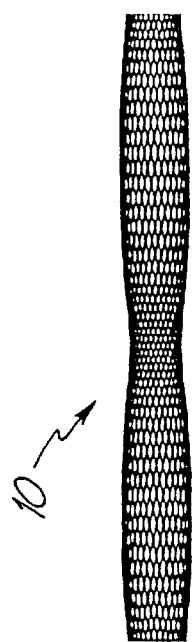

The present invention provides a reproducible, relatively inexpensive method of forming devices for use in occluding aneurysms and the like, as well as devices which may be made via that method. In forming a medical device via the method of the invention, a metal fabric 10 is provided. The fabric is formed of a plurality of wire strands having a predetermined relative orientation between the strands. FIGS. 1A and 1B illustrate two examples of metal fabrics which are suitable for use in the method of the invention.

In the fabric of FIG. 1A, the metal strands define two sets of essentially parallel generally helical strands, with the strands of one set having a "hand", i.e. a direction of rotation, opposite that of the other set. This defines a generally tubular fabric, known in the fabric industry as a tubular braid. Such tubular braids are well known in the fabric arts and find some applications in the medical device field as tubular fabrics, such as in reinforcing the wall of a guiding catheter. As such braids are well known, they need not be discussed at length here.

The pitch of the wire strands (i.e. the angle defined between the turns of the wire and the axis of the braid) and the pick of the fabric (i.e. the number of turns per unit length) may be adjusted as desired for a particular application. For example, if the medical device to be formed is to be used to occlude the channel in which it is placed, the pitch and pick of the fabric will tend to be higher than if the device is simply intended to filter bodily fluid passing therethrough.

For example, in using a tubular braid such as that shown in FIG. 1A to form a device such as that illustrated in FIGS. 5A and 5B, a tubular braid of about 4 mm in diameter with a pitch of about 500 and a pick of about 74 (per linear inch) is believed to be suitable for devices used in occluding aneurysms on the order of about 2 mm to about 4 mm in inner diameter, as detailed below in connection with the embodiment of FIGS. 5A and 5B. Although the exact parameters which define a suitable aneurysm occluder of the invention have not been defined, it is believed that increasing the number of wires used to weave the braid may provide a device which will fill and occlude (or at least occlude) the aneurysm more quickly. Investigations are currently being initiated into the use of a 144-strand wire braid using wires less than a mil in diameter—e.g. 0.00075 inches (about 20 microns) in diameter - which are expected to fairly quickly occlude the neck of the aneurysm and better anchor the occluder in place.

FIG. 1B illustrates another type of fabric which is suitable for use in the method of the invention. This fabric is a more conventional fabric and may take the form of a flat woven sheet, knitted sheet or the like. In the woven fabric shown in FIG. 1B, there are also two sets 14 and 14' of generally parallel strands, with one set of strands being oriented at an angle, e.g. generally perpendicular (having a pick of about 90°), with respect to the other set. As noted above, the pitch and pick of this fabric (or, in the case of a knit fabric, the pick and the pattern of the knit, e.g. Jersey or double knits) may be selected to optimize the desired properties of the final medical device.

The wire strands of the metal fabric used in the present method should be formed of a material which is both resilient and can be heat treated to substantially set a desired shape. Materials which are believed to be suitable for this purpose include a cobalt-based low thermal expansion alloy referred to in the field as Elgiloy, nickel-based high-temperature high-strength "superalloys" commercially available from Haynes International under the trade name Hastelloy, nickel-based heat treatable alloys sold under the name Incoloy by International Nickel, and a number of different grades of stainless steel. The important factor in choosing a suitable material for the wires is that the wires retain a suitable amount of the deformation induced by the molding surface (as described below) when subjected to a predetermined heat treatment.

One class of materials which meet these qualifications are so-called shape memory alloys. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing.

One particularly preferred shape memory alloy for use in the present method is nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here. For example, U.S. Pat. No. 5,067,489 (Lind) and U.S. Pat. No. 4,991,602 (Amplatz et al.), the teachings of which are incorporated herein by reference, discuss the use of shape memory NiTi alloys in guidewires. Such NiTi alloys are preferred, at least in part, because they are commercially available and more is known about handling such alloys than other known shape memory alloys. NiTi alloys are also very elastic—they are said to be "superelastic" or "pseudoelastic". This elasticity will help a device of the invention return to a present expanded configuration for deployment.

The wire strands can comprise a standard monofilament of the selected material, i.e. a standard wire stock may be used. If so desired, though, the individual wire strands may be formed from "cables" made up of a plurality of individual wires. For example, cables formed of metal wires where several wires are helically wrapped about a central wire are commercially available and NiTi cables having an outer diameter of 0.003 inches or less can be purchased. One advantage of certain cables is that they tend to be "softer" than monofilament wires having the same diameter and formed of the same material. Additionally, the use of a cable can increase the effective surface area of the wire strand, which will tend to promote thrombosis.

In preparation of forming a medical device in keeping with the invention, an appropriately sized piece of the metal fabric is cut from the larger piece of fabric which is formed, for example, by braiding wire strands to form a long tubular braid. The dimensions of the piece of fabric to be cut will depend, in large part, upon the size and shape of the medical device to be formed therefrom.

When cutting the fabric to the desired dimensions, care should be taken to ensure that the fabric will not unravel. In the case of tubular braids formed of NiTi alloys, for example, the individual wire strands will tend to return to their heat-set configuration unless constrained. If the braid is heat treated to set the strands in the braided configuration, they will tend to remain in the braided form and only the ends will become frayed. However, it may be more economical to simply form the braid without heat treating the braid since the fabric will be heat treated again in forming the medical device, as noted below.

In such untreated NiTi fabrics, the strands will tend to return to their unbraided configuration and the braid can unravel fairly quickly unless the ends of the length of braid cut to form the device are constrained relative to one another. One method which has proven to be useful to prevent the braid from unraveling is to clamp the braid at two locations and cut the braid to leave a length of the braid having clamps (15 in FIG. 2) at either end, thereby effectively defining an empty space within a sealed length of fabric. These clamps 15 will hold the ends of the cut braid together and prevent the braid from unraveling.

Alternatively, one can solder, braze, weld or otherwise affix the ends of the desired length together (e.g. with a biocompatible cementitious organic material) before cutting the braid. Although soldering and brazing of NiTi alloys has proven to be fairly difficult, the ends can be welded together, such as by spot welding with a laser welder.

The same problems present themselves when a flat sheet of fabric such as the woven fabric shown in FIG. 1B is used. With such a fabric, the fabric can be inverted upon itself to form a recess or depression and the fabric can be clamped about this recess to form an empty pocket (not shown) before the fabric is cut. If it is desired to keep the fabric in a generally flat configuration, it may be necessary to weld the junctions of the strands together adjacent the periphery of the desired piece of fabric before that piece is cut from the larger sheet. So connecting the ends of the strands together will prevent fabrics formed of untreated shape memory alloys and the like from unraveling during the forming process.

Once an appropriately sized piece of the metal fabric is obtained, the fabric is deformed to generally conform to a surface of a molding element. As will be appreciated more fully from the discussion below in connection with FIGS. 2–6, so deforming the fabric will reorient the relative positions of the strands of the metal fabric from their initial order to a second, reoriented configuration. The shape of the molding element should be selected to deform the fabric into substantially the shape and size of the desired medical device.

The molding element can be a single piece, or it can be formed of a series of mold pieces which together define the surface to which the fabric will generally conform. The molding element can be positioned within a space enclosed by the fabric or can be external of such a space, or can even be both inside and outside such a space.

Figure 2:
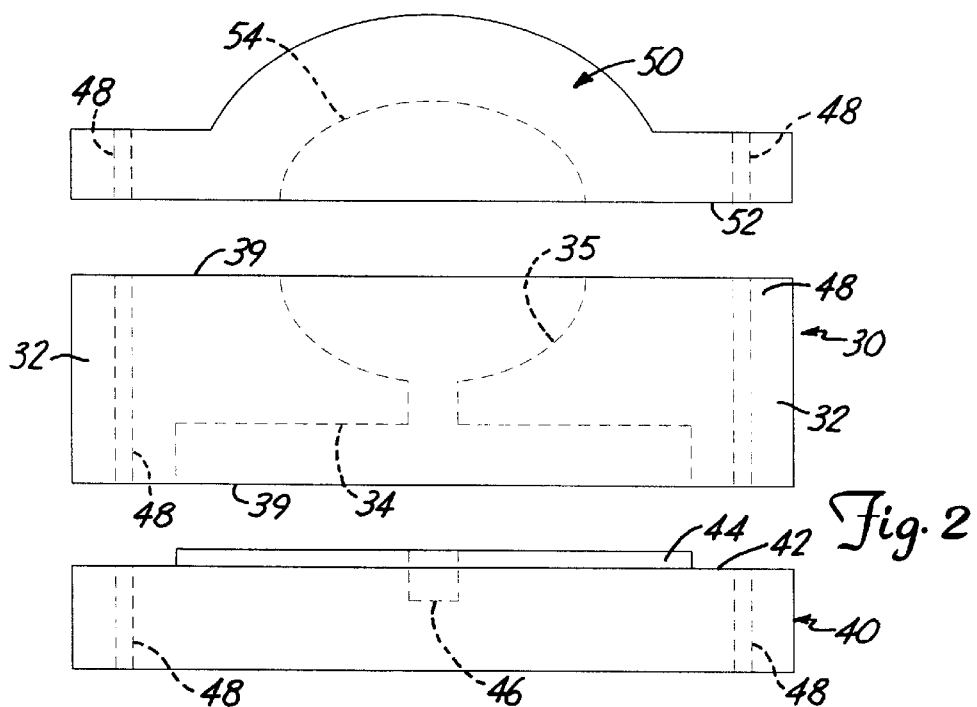
FIG. 2 is a side view of a molding element and a length of a metal fabric suitable for use in forming a medical device in accordance with the invention, the mold being in a disassembled state.
Figure 3:
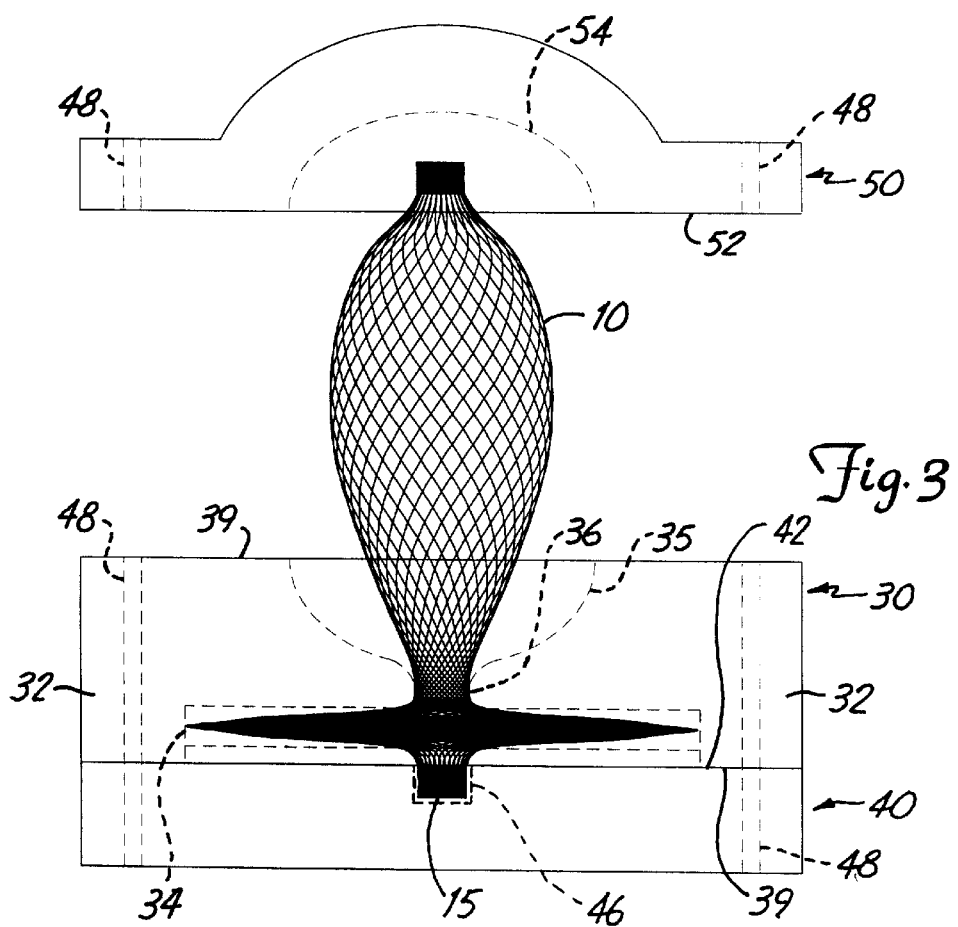
FIG. 3 is a side cross sectional view showing the molding element and metal fabric of FIG. 2 in a partially assembled state.
Figure 4:
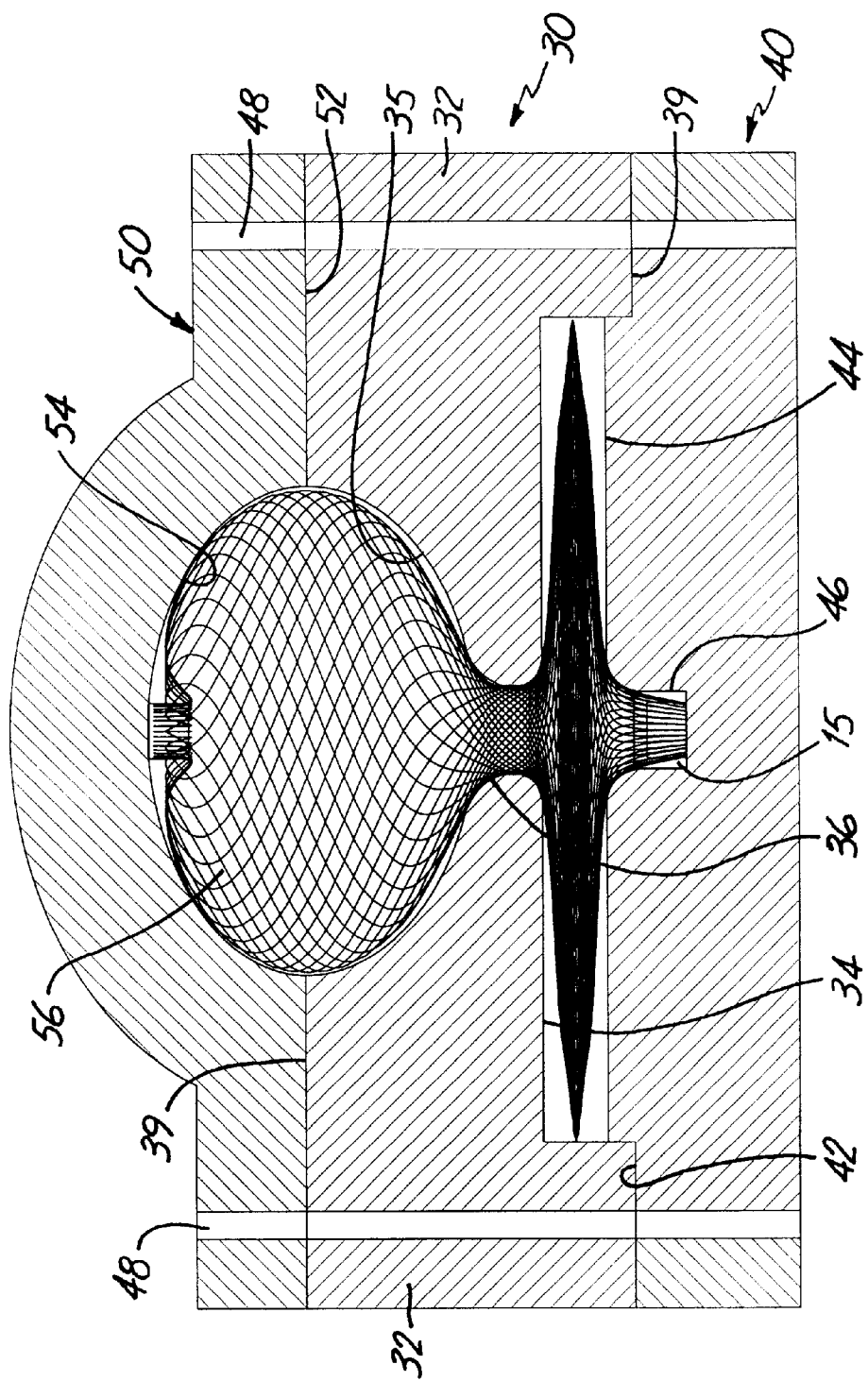
FIG. 4 is a side cross-sectional view showing the molding element and metal fabric of FIG. 2 in an assembled state.

In order to illustrate one example of how such a mold may be configured and how it may be used in accordance with the method of the invention, reference will be had to FIGS. 2–6. In FIGS. 2–4, the molding element 20 is formed of a number of separate pieces which can be attached to one another complete the molding element 20. In using such a multi-piece molding element, the mold can be assembled about the cut length of fabric 10, thereby deforming the fabric to generally conform to the desired surface (or surfaces) of the molding element.

In the molding element illustrated in FIGS. 2–4, the metal fabric 10 is deformed to generally conform to a surface of the molding element 20, the molding element comprising a center section 30 and a pair of end plates 40, 50. Turning first to the center section 30, the center section is desirably formed of opposed halves 32, 32 which can be moved away from one another in order to introduce the metal fabric 10 into the mold. Although these two halves 32, 32 are shown in the drawings as being completely separated from one another, it is to be understood that these halves could be interconnected, such as by means of a hinge or the like, if so desired.

The opposed halves 32, 32 of the molding element 20 shown in the drawings of FIGS. 2–4 each include a pair of recesses opposed on either side of a ridge defining a generally semi-circular opening. When the two halves are assembled in forming the device, as best seen in FIGS. 3 and 4, the semicircular openings in the opposed halves 32, 32 mate to define a generally circular forming port 36 passing through the center section 30. Similarly, the recesses in the two halves together form a pair of central recesses 34, 35 with one such recess being disposed on either face of the center section. The lower central recess 34 may be relatively shallow and generally cylindrical while the upper central recess 35 may be a little deeper and generally upwardly concave.

The overall shape and dimensions of the center section can be varied as desired; it is generally the size of the central recesses 34 and the forming port 36 which will define the size and shape of the middle of the finished device, as explained below. If so desired, each half 32 may be provided with a manually graspable projection (not shown). For example, such a projection may be provided at a location disposed away from the abutting faces of the respective halves to enable an operator to more easily join the two halves to define the recesses 34, 35 and forming port 36.

The center section is adapted to cooperatively engage a pair of end plates 40, 50 for forming the desired device. In the embodiment shown in FIGS. 2 and 3, the center section 30 has a pair of flat outer faces 39 which are each adapted to be engaged by an inner face 42, 52 of one of the two end plates. The lower end plate 40 includes a compression disk 44 which extends generally laterally upwardly (in FIGS. 2–4) from the inner face 42 of the end plate. This compression disk 44 should be sized to permit it to be received within the lower central recesses 34 of the center section 30, as shown in FIGS. 3 and 4. For reasons explained more fully below, the compression disk 44 includes a cavity 46 for receiving an end of the length of the metal fabric 10.

In the embodiment illustrated in FIGS. 2–4, the upper end plate 50 has a downwardly concave recess 54 formed therein. This recess is desirably generally circular in horizontal cross section and may be generally hemispherical in overall shape. The bottom of the recess 54 optimally defines a generally circular opening in the inner face 52 of the end plate. This opening is desirably formed to be of about the same size and shape as the opening in the adjacent outer face 39 of the center section defined by the upper central recess 35. When the mold is assembled, as described below, the recesses 35 and 54 together define an upper chamber for forming an upper length of the metal fabric.

One or more channels 48 for receiving bolts and the like may also be provided through each of the end plates and through the center section 30. By passing bolts (not shown) through these channels 48, one can assemble the molding element 20 and retain the metal fabric in the desired shape during the heat treatment process, as outlined below.

In utilizing the molding element 20 shown in FIGS. 2–4, a length of the metal fabric 10 can be positioned between the opposed halves 32 of the center section 30. In the drawings of the molding element 20 of FIGS. 2–4, the metal fabric 10 is a tubular braid such as that illustrated in Figure IA. A sufficient length of the tubular braid should be provided to permit the fabric to conform to the molding surface, as explained below. Also, as noted above, care should be taken to secure the ends of the wire strands defining the tubular braid in order to prevent the metal fabric from unraveling.

A length of the metal braid may be positioned within one of the two halves of the forming port 36 and the opposed halves 32 of the center section may be joined to abut one another to restrain a central portion of the metal braid within the central forming port 36 through the center section. For reasons made clearer in the following discussion, the fabric is desirably positioned in the forming port with a greater length of the fabric extending above the center section 30 than extends below the center section.

The tubular braid will tend to have a natural, relaxed diameter which is defined, in large part, when the tubular braid is formed. Unless the tubular braid is otherwise deformed, when the wire strands are in their relaxed state they will tend to define a generally hollow tube having the predetermined diameter. The outer diameter of the relaxed braid may be, for example, about 4 mm. The relative size of the forming port 36 in the central section 30 of the molding element and the natural, relaxed outer diameter of the tubular braid may be varied as desired to achieve the desired shape of the aneurysm occlusion device being formed.

In the embodiment shown in FIGS. 2 and 3, the inner diameter of the forming port 36 is optimally slightly less than the natural, relaxed outer diameter of the tubular braid 10. Hence, when the two halves 32, 32 are assembled to form the center section 30, the tubular braid 10 will be slightly compressed within the forming port 36. This will help ensure that the tubular braid conforms to the inner surface of the forming port 36, which defines a portion of the molding surface of the molding element 20.

If so desired, a generally cylindrical internal molding section (not shown) may also be provided. This internal molding section has a slightly smaller diameter than the inner diameter of the forming port 36. In use, the internal molding section is placed within the length of the metal fabric, such as by manually moving the wire strands of the fabric apart to form an opening through which the internal molding section can be passed. This internal molding section should be positioned within the tubular braid at a location where it will be disposed within the forming port 36 of the center section when the molding element is assembled. There should be a sufficient space between the outer surface of the interior molding section and the inner surface of the forming port 36 to permit the wire strands of the fabric 10 to be received therebetween.

By using such an internal molding section, the dimensions of the central portion of the finished medical device can be fairly accurately controlled. Such an internal molding section may be necessary in circumstances where the natural, relaxed outer diameter of the tubular braid 10 is less than the inner diameter of the forming port 36 to ensure that the braid conforms to the inner surface of that forming port. However, it is not believed that such an internal molding section would be necessary if the natural, relaxed outer diameter of the braid were larger than the inner diameter of the forming port 36.

As noted above, the ends of the tubular braid should be secured in order to prevent the braid from unraveling. The lower end of the metal fabric 10 is desirably received within a cavity 46 formed in the lower end plate 40. If a clamp (15 in FIGS. 3 and 4) is used, the clamp may be sized to be relatively snugly received within this cavity 46 in order to effectively attach the end of the fabric to the end plate 40. The lower end plate can then be urged toward the center section 30 until the compression disk 44 is received within the lower central recess 34 of the center section 30, as shown in FIG. 3.

Figure 5A:
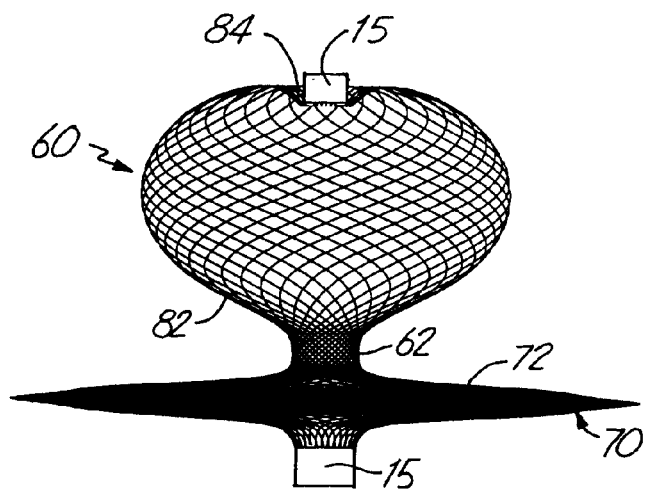
FIGS. 5A and 5B are schematic side cross sectional illustrations of two alternative embodiments of aneurysm occlusion devices in accordance with the invention.
Figure 5B:
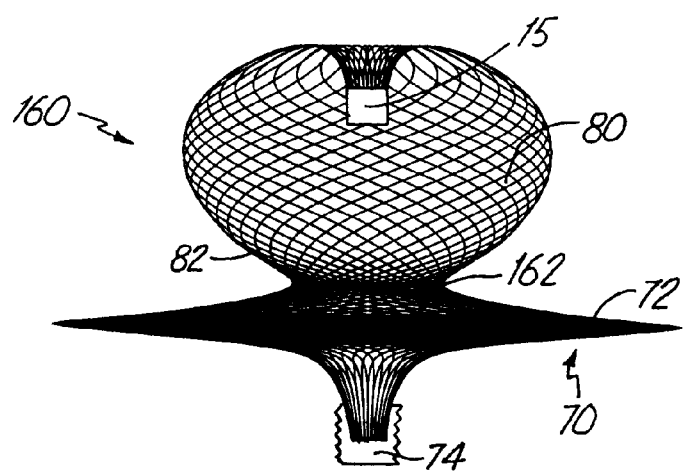
Figure 6:
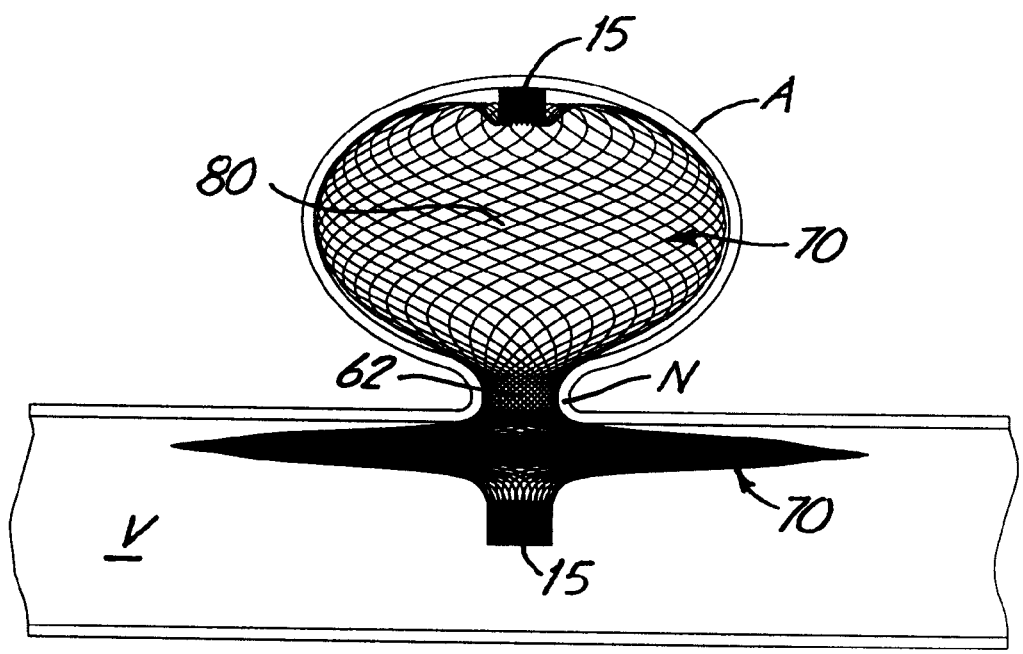
FIG. 6 is a schematic illustration showing the device of FIG. 5A deployed to occlude an aneurysm in a channel of a patient's vascular system.

As shown in FIGS. 5-6, receiving the clamp in a recess yields a final device wherein the clamp 15 is exposed. For reasons discussed more fully below, having such a projection on the aneurysm-filling portion of the device is not desirable. Accordingly, the upper end plate 50 desirably does not include a recess for receiving any clamp which may be placed on the upper end of the metal fabric. Instead, the metal fabric is simply generally directed into the downwardly concave recess 54 of the upper end plate and the upper end plate is moved toward the center section 30 until the faces 52, 39 of these two mold elements abut one another. This defines a bulbous, rounded cavity 56 within which the upper length of the metal fabric is received. The molding element may then be clamped in position by passing bolts or the like through the channels 48 in the molding element and locking the various components of the molding element together by tightening a nut down onto such a bolt (not shown).

Care should be taken to ensure that the fabric generally remains within the cavity defined by the recesses 35, 54, i.e. to avoid pinching the fabric between the faces 52, 39. If it proves to be unnecessarily difficult to properly position the upper length of the metal fabric within this cavity, a support structure (not shown) for the clamp 15 on the end of the metal fabric. For example, a small tube could descend generally axially downwardly (in the orientation of FIGS. 2–4) from the top center of the recess 54 and the interior of the tube can be sized to fairly snugly receive the clamp 15. This tube should not be too long; a length approximately equal to or less than the length of the clamp 15 would be preferred. This will serve much the same function as that served by the recess 46 in the lower end plate and help keep the fabric properly aligned during assembly of the molding element 20.

As best seen in FIG. 3, when an end plate 40, 50 is urged toward the center section 30, this will compress the tubular braid 10 generally along its axis. When the tubular braid is in its relaxed configuration, as illustrated in FIG. 1A, the wire strands forming the tubular braid will have a first, predetermined relative orientation with respect to one another. As the tubular braid is compressed along its axis, the fabric will tend to flare out away from the axis, as illustrated in FIGS. 3 and 4. When the fabric is so deformed, the relative orientation of the wire strands of the metal fabric will change. When the molding element is finally assembled, the metal fabric will generally conform to the molding surface of this element.

In the molding element 20 shown in FIGS. 2–4, the molding surface is defined by the inner surface of the forming port, the inner surfaces of the central recesses 34, 35, the face of the compression disk 44 in the recess 34, and the downwardly concave recess 54 of the upper plate 50. If an internal molding section is used, the cylindrical outer surface of that section may also be considered a part of the molding surface of the molding element 20. Accordingly, when the molding element 20 is completely assembled the metal fabric between the relatively closely positioned compression disk 44 and the top of the recess 34 will define a relatively thin, perhaps even disk-like shape. The fabric positioned in the chamber 56 will tend to conform to the larger, more bulbous shape of the cavity. A relatively narrow center section connects the lower disc shape with the more bulbous portion. As the inner surface area of the cavity 56 is greater than the surface area defined by the compression disc 44 and the recess 34, the portion of the fabric extending above the port 36 should be longer than the portion extending below that port, as noted above.

It should be understood that the specific shape of the particular molding element 20 shown in FIGS. 2-4 is intended to produce one useful medical device in accordance with the invention, but that other molding elements having different configurations could also be used. If a more complex shape is desired, the molding element may have more parts, but if a simpler shape is being formed the molding element may have even fewer parts. The number of parts in a given molding element and the shapes of those parts will be dictated almost entirely by the shape of the desired aneurysm occlusion device as the molding element must define a molding surface to which the metal fabric will generally conform.

Accordingly, the specific molding element 20 shown in FIGS. 2–4 is simply intended as one specific example of a suitable molding element for forming one particular useful medical device. Depending on the desired shape of the medical device being formed, the shape and configuration of other specific molding elements can be readily designed by those of ordinary skill in the art.

Once the molding element 20 is assembled with the metal fabric generally conforming to a molding surface of that element, the fabric can be subjected to a heat treatment while it remains in contact with that molding surface. This heat treatment will depend in large part upon the material of which the wire strands of the metal fabric are formed, but the time and temperature of the heat treatment should be selected to substantially set the fabric in its deformed state, i.e., wherein the wire strands are in their reoriented relative configuration and the fabric generally conforms to the molding surface.

The time and temperature of the heat treatment can vary greatly depending upon the material used in forming the wire strands. As noted above, one preferred class of materials for forming the wire stands are shape memory alloys, with nitinol, a nickel titanium alloy, being particularly preferred. If nitinol is used in making the wire strands of the fabric, the wire strands will tend to be very elastic when the metal is in its austenitic phase; this very elastic phase is frequently referred to as a "superelastic" or "pseudoelastic"

phase. By heating the nitinol above a certain phase transition temperature, the crystal structure of the nitinol metal when in its austenitic phase can be set. This will tend to "set" the shape of the fabric and the relative configuration of the wire strands in the positions in which they are held during the heat treatment.

Suitable heat treatments of nitinol wire to set a desired shape are well known in the art. Spirally wound nitinol coils, for example, are used in a number of medical applications, such as in forming the coils commonly carried around distal lengths of guidewires. A wide body of knowledge exists for forming nitinol in such medical devices, so there is no need to go into great detail here on the parameters of a heat treatment for the nitinol fabric preferred for use in the present invention.

Briefly, though, it has been found that holding a nitinol fabric at about 500° C. to about 550° C. for a period of about 1 to about 30 minutes, depending on the softness or harness of the device to be made, will tend to set the fabric in its deformed state, i.e. wherein it conforms to the molding surface of the molding element. At lower temperatures the heat treatment time will tend to be greater (e.g. about one hour at about 350° C.) and at higher temperatures the time will tend to be shorter (e.g. about 30 seconds at about 900° C.). These parameters can be varied as necessary to accommodate variations in the exact composition of the nitinol, prior heat treatment of the nitinol, the desired properties of the nitinol in the finished article, and other factors which will be well known to those skilled in this field.

Instead of relying on convection heating or the like, it is also known in the art to apply an electrical current to the nitinol to heat it. In the present invention, this can be accomplished by, for example, hooking electrodes to the clamps 15 carried at either end of the metal fabric illustrated in FIG. 2. The wire can then be heated by resistance heating of the wires in order to achieve the desired heat treatment, which will tend to eliminate the need to heat the entire molding element to the desired heat treating temperature in order to heat the metal fabric to the desired temperature.

After the heat treatment, the fabric is removed from contact with the molding element and will substantially retain its shape in a deformed state. When the molding element 20 illustrated in FIGS. 2–4 is used, the various parts of the molding element may be disassembled in essentially the reverse of the process of assembling the molding element. If an internal molding section is used, this molding section can be removed in much the same fashion that it is placed within the generally tubular metal fabric in assembling the molding element 20, as detailed above. The device can then be collapsed, such as by urging the clamps generally axially away from one another, which will tend to collapse the device toward its axis. The collapsed device 80 can then be passed through a catheter for deployment in an aneurysm, as detailed below.

FIGS. 5A and 5B schematically illustrate two possible embodiments of an aneurysm occlusion device 60 in accordance with the invention. The embodiment of FIG. 5A generally corresponds to the shape of a device which may be made using the molding element 20 of FIGS. 2–4. The device 160 of FIG. 5B is fairly similar to the device 60 of FIG. 5A, with some specific modifications discussed below. Given the above explanation of the molding element 20 and the resulting device 60, it should be clear how to make a suitable mold and form a device as shown in FIG. 5B. As discussed below, the devices of FIG. 5 are particularly well suited for use in occluding an aneurysm or the like in a channel within a patient's body and these designs have particular advantages in use as aneurysm occlusion devices.

The vascular occlusion device 60 of FIG. 5A includes a generally tubular central portion 62 disposed between an anchor 70 and a body portion 80. The anchor and the body portion desirably have substantially larger diameters than does the central portion. The anchor desirably increases in diameter relatively rapidly moving away from the central portion such that the inner surface 72 of the anchor defines a shoulder facing generally inwardly toward the central portion 62. The body portion 80 also desirably increase relatively rapidly in diameter moving away from the central portion 62 to define a shoulder 82, though a more gradual slope on this surface is believed to be acceptable.

As described below in connection with FIG. 6, this permits the central portion of the occluder to be received within the neck of the aneurysm while the body portion is received within the aneurysm and the anchor remains in the lumen of the affected vessel. The size ratios of these three elements 62, 70 and 80 can be varied to meet specific needs, but for most circumstances it seems likely that the body portion will define a larger volume, and will likely have a larger surface area, than will the anchor.

The size of the occluder 60 can be varied as desired to occlude different types of lateral aneurysms. For example, to occlude relatively small berry aneurysms in cranial arteries, the occluder will likely be relatively small; to occlude significantly larger aneurysms in larger vessels, a larger occluder should be used.

In the embodiment of FIG. 5A, the occluder 60 has a clamp 15 at either end of the metal fabric used to form the device. The clamp 15 attached to the anchor 70 can protrude downwardly beyond the outer end of the anchor without any ill effects. Due to the improvements in manufacturing process noted above, this is likely a preferred structure.

The clamp 15 at the other end of the metal fabric, i.e. the clamp attached to the body portion 80 of the occluder, desirably does not extend beyond the curvature of the surface of the body portion. In the embodiment of FIG. 5A, the fabric is indented downwardly to define a recess 84 so that the top of the clamp 15 extends only slightly above the top of the rest of the body portion. If the clamp were to extend substantially beyond the rest of the body portion 80, this would present the body portion with a hard, relatively traumatic projection. As such a projection could damage the wall of the aneurysm during deployment, it is desired to reduce the profile of the clamp.

The clamp of the body portion of the device of FIG. 5A extends slightly above the top of the fabric due to the generally hemispherical shape of the recess 54 of the molding element 20. If one desired to eliminate such a protrusion altogether, one could slightly alter the shape of the recess 54. In particular, rather than continuing the smooth curvature of the recess, the very apex of the recess, i.e. the point farthest removed from the central element 30 of the mold, can be flattened out somewhat. The clamp 15 will then abut this flat area and the rest of the fabric can curve upwardly to abut this flat area before it begins to follow the curvature of the rest of the recess 54.

The shapes of the body and the anchor can be varied as desired. For example, some lateral aneurysms are not smooth, nearly spherical structures as shown in FIG. 6, but are instead somewhat irregular. Although one may ideally make the body about the same size and shape as the aneurysm, this is likely unnecessary and highly impractical.

For most applications, it is believed that occluders 60 with relatively hemispherical body portions 80, as illustrated, will be broadly useful and may be acceptable for virtually any aneurysm due to the flexible nature of the metal fabric. It may be desirable, nonetheless, to have some while others are formed with more elliptically shaped body portions, and others have even more complex geometries.

FIG. 5B illustrates an occluder 160 which shares most of the same elements as the occluder 60 of FIG. 5A. In particular, the occluder 160 includes a body portion 80 having an inwardly facing shoulder 82, an anchor 70 having an inwardly facing shoulder 72, and a clamps at either end of the fabric used to form the device.

The middle of the device 160 differs from the central portion 62 of the occluder 60, though. Instead of having a distinct, readily identifiable length of fabric which can be identified as the central portion 62, the central portion 162 of FIG. 5B is much shorter. In fact, the central portion may be defined as little more than a location where the body portion 80 adjoins the anchor 70. Nonetheless, when the occluder is deployed in an aneurysm as outlined below in connection with FIG. 6, this shortened central portion is desirably positioned within the neck of the aneurysm much as is the central portion 62 of the occluder shown inn FIG. 6.

The anchors 70 of FIGS. 5A and 5B are both shown as being relatively flat, with adjacent sides of the anchor being immediately adjacent one another. If so desired, though, the anchor is instead curved slightly so that it is downwardly somewhat concave. If the degree of curvature is about the same as that of the curvature of the inner wall of the vessel adjacent the aneurysm the device is to treat, it is believed that this will help better seat the occluder 160 in the aneurysm. One could form the anchor so that, rather than being uniformly and symmetrically curved, it is curved to define a longer arc, i.e. to more closely follow the cylindrical shape of the vessel wall, and further assist in seating the occluder.

As detailed above, in making a device of the invention it is desirable to attach the ends of the wire strands forming the metal fabric 10 to one another to prevent the fabric from unraveling. In the illustrations of FIGS. 2–4, a clamp 15 is used to tie together the ends of the wire strands. It is to be understood that this clamp 15 is simply a schematic illustration, though, and that the ends could be attached in other ways, such as by welding, soldering, brazing, use of a biocompatible cementitious material or in any other suitable fashion.

The clamp 74 of the anchor 70 in FIG. 5B differs from the relatively smooth clamp 15 attached to the anchor of FIG. 5A. This clamp 74 serves the same purpose as the schematically illustrated clamp 15, namely to interconnect the ends of the wires. However the clamp 74 also serves to connect the device 160 to a delivery system (not shown). In the embodiment shown, the clamp 74 is generally cylindrical in shape and has a recess for receiving the ends of the wires to substantially prevent the wires from moving relative to one another, and a threaded outer surface. The threaded outer surface is adapted to be received within a cylindrical recess (not shown) on a distal end of a delivery device and to engage the threaded inner surface of the delivery device's recess.

A delivery device (not shown) for delivering the occluder 160 can take any suitable shape, but desirably comprises an elongate, flexible metal shaft having such a recess at its distal end. The delivery device can be used to urge the aneurysm occlusion device 160 through the lumen of a catheter for deployment in an aneurysm in a channel of the patient's body, as outlined below. When the device is deployed out the distal end of the catheter, the device will still be retained by the delivery device. Once the proper position of the device 60 or 160 in the aneurysm is confirmed, the shaft of the delivery device can be rotated about its axis to unscrew the clamp 74 from the recess in the delivery means.

By keeping the aneurysm occlusion device 160 attached to the delivery means, the operator could still retract the device for repositioning if it is determined that the device is not properly positioned in the first attempt. This threaded attachment will also allow the operator to control the manner in which the device 160 is deployed out of the distal end of the catheter. As explained below, when the device exits the catheter it will tend to resiliently return to a preferred expanded shape which is set when the fabric is heat treated. When the device springs back into this shape, it may tend to act against the distal end of the catheter, effectively urging itself forward beyond the end of the catheter. This spring action could conceivably result in improper positioning of the device. Since the threaded clamp 74 can enable the operator to maintain a hold on the device during deployment, the spring action of the device can be controlled and the operator can control the deployment to ensure proper positioning.

The manner in which the fabric on the upper end of the body portion 80 is clamped in the occluder 160 of FIG. 5B also differs somewhat from the way in which the clamp 15 of the body portion of the occluder 60 of FIG. 5A is arranged. As noted above, the clamp 15 in FIG. 5A is received in a recess 84 of the body portion to reduce trauma to the aneurysm. Instead, the clamp 15 in FIG. 5B is received generally within the rest of the body portion. Effectively enclosing the clamp within the body portion in this fashion further reduces the risk of trauma to the aneurysm during deployment because the fabric of the body portion will stand between the clamp 15 and the aneurysm.

The enclosed clamp structure of FIG. 5B can be formed by inverting the tubular fabric inwardly on itself, much like turning a sock inside out. In order to keep the fabric from unraveling, it may be necessary to fix the wires with respect to one another at both ends of the length of fabric before inverting the tube. In order to make this possible, it may be necessary to clamp one end using the clamp 15 and use a temporary, generally annular clamp at the other end of the fabric. This clamp may take the form of a pair of rings, one within the other, not unlike an embroidery hoop used in embroidery. Alternatively, a ring of a cementitious material can be used or overlapping wires can be spot welded to one another.

Once the fabric is inverted so the clamp 15 is positioned within the fabric, the other end of the fabric can be clamped with a similar clamp or the clamp 74 shown in FIG. 5B. The rest of the manufacturing process can then be carried our generally as outlined above in connection with FIGS. 2–4.

The pick and pitch of the metal fabric 10 used in forming the occluder 60, as well as some other factors such as the number of wires employed in a tubular braid, are important in determining a number of the properties of the device. For example, the greater the pick and pitch of the fabric, and hence the greater the density of the wire strands in the fabric, the stiffer the device will be. Having a greater wire density will also provide the device with a greater wire surface area, which will generally enhance the tendency of the device to occlude the aneurysm in which it is deployed. As noted above, it may be possible to form a metal fabric having as many as 144 individual wire strands formed of wire under 1 mil thick. So increasing the number of wires and using a smaller wire also tends to increase the surface area of the wire, which is believed to enhance the thrombogenicity of the device and occlude an aneurysm more quickly.

When the device is deployed in a patient's vessel, thrombi will tend to collect on the surface of the wires. By having a greater wire density, the total surface area of the wires will be increased, increasing the thrombolytic activity of the device and permitting it to relatively rapidly occlude the aneurysm in which it is deployed. It is believed that forming the occlusion device 60 from a 4 mm diameter tubular braid having a pick of at least about 40 and a pitch of at least about 30° will provide sufficient surface area to substantially completely occlude a an aneurysm of 2 mm to about 4 mm in inner diameter in a suitable period of time.

The thrombogenicity of the occluder can be enhanced, e.g. by a coating of a thrombolytic agent or by attaching silk or wool fabric to the device. A variety of materials and techniques for enhancing or reducing thrombogenicity are well known in the art and need not be detailed here. It is not clear that rapidly closing the neck of the aneurysm is always desirable, though. There is some speculation that it may be better to close off an aneurysm more slowly, allowing the pressure in the aneurysm to decrease, thereby shrinking the aneurysm and reducing stress on the distended vessel wall. If so desired, a more loosely woven (or knitted, etc.) fabric may be employed. The patency of the neck of the aneurysm can be further prolonged by treating part or all of the device with a coating of a lubricious, antithrombogenic compound; a variety of such materials are known in the art and are commercially available.

FIG. 6 schematically illustrates how a medical device 60 generally as outlined above can be used to occlude an aneurysm. In this case, a lateral aneurysm A is defined as a bulge in the vessel wall, with a neck N communicating the interior of the aneurysm with the lumen of the vessel V. The presence and size an aneurysm, and perhaps also its general shape, can be determined by known diagnostic techniques. Once an aneurysm has been identified and the suitability of the present invention for treating the aneurysm has been confirmed, the operator will need to select an appropriately sized occluder 60 (or 160, as desired) to treat the specific aneurysm.

Occluders made in accordance with the method of the invention outlined above have a preset expanded configuration and a collapsed configuration which allows the device to be passed through a catheter. The expanded configuration is generally defined by the shape of the metal fabric when it is deformed to generally conform to the molding surface of the molding element. Heat treating the metal fabric substantially sets the shapes of the wire strands in the reoriented relative positions when the fabric conforms to the molding surface. When the metal fabric is then removed from the molding element, the fabric may define a medical device in its preset expanded configuration.

The medical device can be collapsed into its collapsed configuration and inserted into the lumen of the catheter. The collapsed configuration of the device may be of any shape suitable for easy passage through the lumen of a catheter and proper deployment out the distal end of the catheter. For example, the devices shown in FIGS. 5 may have a relatively elongated collapsed configuration wherein the devices are stretched along their axes. This collapsed configuration can be achieved simply by stretching the device generally along its axis, e.g. by manually grasping the clamps 15 (or 15, 74) and pulling them apart, which will tend to collapse the expanded body portion and the anchor of the device inwardly toward the device's axis. In this regard, these devices 60 and 160 are not unlike "Chinese handcuffs", which tend to constrict in diameter under axial tension.

The medical device is collapsed and inserted into the catheter and the distal end of the catheter is desirably positioned within the aneurysm. (These two steps can be performed in any order.) The occluder 60 can be urged along the lumen of the catheter toward the distal end of the catheter, such as by using a guidewire or the like to abut against the device and urge it along the catheter. When the device begins to exit the distal end of the catheter, which is positioned adjacent the desired treatment site, it will tend to resiliently return substantially entirely to its preset expanded configuration. Superelastic alloys, such as nitinol, are particularly useful in this application because of their ability to readily return to a particular configuration after being elastically deformed to a great extent.

As noted above, the body portion is desirably larger than the neck N of the aneurysm A. The occluder 60 can then be retracted so that the inwardly facing shoulder 82 of the body portion engages the wall of the aneurysm. If one continues to retract the catheter, the engagement of the occluder with the wall of the aneurysm will tend to naturally pull the rest of the occluder out of the catheter, permitting it to return to its expanded configuration. Care should be taken to position the distal end of the catheter within the lumen of the vessel V before the anchor exits the catheter. This will ensure that the anchor is seated within the lumen rather than being lodged in the aneurysm with the rest of the device. Although such an inaccurate deployment of the occluder 60 entirely within the aneurysm should not have any adverse consequences, the benefit of the occluder's unique feature and design will not be fully realized.

The body portion should be sized so that it is larger than the neck N of the aneurysm A, as noted above. In a preferred embodiment, the body portion is large enough so that it can expand to fill a majority of the aneurysm and, optimally, is large enough to bring the metal fabric into contact with substantially the entire interior surface of the aneurysm. It is believed that making the body portion too large for the aneurysm may prevent the central portion 62 from being properly positioned in the neck, though. Hence, it may be better to err on the side of having a body portion which is not quite large enough to fill the aneurysm rather than having a body portion which is too large. (By "filling" the aneurysm, it is to be understood that the fabric of the body portion itself will not actually have a volume sufficient to fill the aneurysm, but rather that the volume within the fabric together with the fabric itself is about the same as the volume of the aneurysm.) When the anchor 70 is deployed in the lumen of the vessel V after deploying the body portion 80 in the aneurysm A, the central portion 62 of the occluder will tend to be automatically positioned in the neck N of the aneurysm. The anchor will typically engage the inner wall of the vessel. As the body portion is larger than the neck N and will resist pulling out of the aneurysm, the occluder will be firmly seated in the aneurysm. Over a relatively short period of time, thrombi will form in and on the occluder 60; the rate of thrombosis can be controlled somewhat by the use of thrombogenic or antithrombogenic agents, as noted above.

The thrombi will tend to occlude the neck of the aneurysm first as this is the narrowest area of the aneurysm and the greatest wire density is present there. The body portion 80 of the occluder will induce thrombosis in the aneurysm itself so that over time substantially the entire volume interior of the aneurysm can be filled with either the fabric of the occluder or thrombi. The present invention, therefore, will achieve generally the same function as the balloons and thrombolytic coils discussed in the background section above, i.e. to fill the aneurysm. It is believed that the present invention may be able to allow an operator to fill an aneurysm more easily and, perhaps, more cost effectively than either of these approaches.

More importantly, though, the present invention has an added advantage not possessed by either of these prior art techniques. It was noted above that operators deploying balloons or filling aneurysms with various other materials frequently also deploy a graft or stent in the vessel to occlude the neck N of the aneurysm. The anchor 70 and central portion 62 of the present invention can achieve much the same end, but does not require the operator to go through two separate deployment procedures to first fill the aneurysm and then separately install a stent or graft. Accordingly, the present invention can be deployed more quickly and more easily than the 2-device approach of the past.

In addition, the anchor 70 of the occluder 60 is only in contact with a fairly localized area of the vessel wall. In contrast, a standard stent or graft is in contact with, and frequently urges outwardly against, a fairly large surface area of the vessel. The present invention thereby minimizes the deleterious effects, noted above, associated with stents in contact with otherwise healthy tissue of the vessel wall.

While a preferred embodiment of the present invention has been described, it should be understood that various changes, adaptations and modifications may be made therein without departing from the spirit of the invention and the scope of the appended claims.

What is claimed is:

1. An aneurysm occlusion device for occluding an aneurysm in a vessel of a patient's body, comprising a bulbous body portion sized to be received within the aneurysm, an anchor sized and shaped to engage an interior 10 surface of the vessel's wall, and a pair of clamps; the body portion and the anchor being integrally formed of a resilient fabric permitting the occlusion device to be collapsed for deployment and resiliently self-expand to occlude the aneurysm; one of said clamps being carried by the anchor, the other of said clamps being carried by and enclosed within an interior of the body portion.

2. The aneurysm occlusion device of claim 1 wherein the resilient fabric is formed of a plurality of wire strands having ends, the clamps securing the ends of the wire strands.

3. The aneurysm occlusion device of claim 1 wherein the interior of the body portion is hollow and defines a recess sized to receive the clamp carried by the body portion to provide the body portion with an atraumatic surface.

4. The aneurysm occlusion device of claim 1 wherein the aneurysm has an enlarged body and a narrowed neck connecting the body to a wall of the vessel, the aneurysm occlusion device further comprising a generally tubular central portion disposed between and connecting the body portion and the anchor, the central portion being sized and shaped to be received within the neck of the aneurysm.

5. A medical occlusion device comprising a body, an anchor and a reduced diameter, generally tubular central portion disposed between and connecting the body and the anchor; the body, the anchor and the central portion being integrally formed of a resilient fabric formed of a plurality of wire strands and permitting the occlusion device to be collapsed for deployment and resiliently self-expand; ends of the wire strands being secured to one another with a first set of secured ends being adjacent the body portion, the first set of secured ends being received within a recess adjacent a top of the body portion, thereby providing the body portion with an atraumatic surface.

6. The aneurysm occlusion device of claim 5 wherein the body has a hollow interior, the recess comprising said hollow interior of the body.

* * * * *